(12) United States Patent
Peters et al.

(10) Patent No.: US 9,133,184 B2
(45) Date of Patent: Sep. 15, 2015

(54) CHROMEN-2-ONE DERIVATIVES AND THEIR USE AS MONOAMINE NEUROTRANSMITTER RE-UPTAKE INHIBITORS

(71) Applicant: ANIONA APS, Farum (DK)

(72) Inventors: Dan Peters, Malmo (SE); Gordon Munro, Skovlunde (GB); Elsebet Ostergaard Nielsen, Kobenhavn K (DK); Karin Sandager Nielsen, Fredensborg (DK)

(73) Assignee: ANIONA APS, Farum (DK)

( * ) Notice: Subject to any disclaimer, the term of this patent is extended or adjusted under 35 U.S.C. 154(b) by 0 days.

(21) Appl. No.: 14/263,664

(22) Filed: Apr. 28, 2014

(65) Prior Publication Data

US 2014/0235669 A1    Aug. 21, 2014

Related U.S. Application Data

(63) Continuation of application No. 13/575,712, filed as application No. PCT/EP2011/050455 on Jan. 14, 2011, now abandoned.

(60) Provisional application No. 61/301,367, filed on Feb. 4, 2010.

(30) Foreign Application Priority Data

Jan. 29, 2010   (DK) .................................. 2010 00079

(51) Int. Cl.
  *A01N 43/42*   (2006.01)
  *A61K 31/44*   (2006.01)
  *C07D 451/06*  (2006.01)

(52) U.S. Cl.
  CPC .................................. *C07D 451/06* (2013.01)

(58) Field of Classification Search
  USPC .......................................... 514/304; 546/126
  See application file for complete search history.

(56) References Cited

U.S. PATENT DOCUMENTS

| | | |
|---|---|---|
| 5,916,914 A | 6/1999 | Connor et al. |
| 6,034,121 A | 3/2000 | O'Mahony et al. |
| 8,697,721 B2 | 4/2014 | Peters et al. |
| 2004/0106645 A1 | 6/2004 | Blackburn et al. |
| 2005/0054681 A1 | 3/2005 | Jackson et al. |
| 2007/0232666 A1 | 10/2007 | Peters et al. |
| 2008/0214820 A1 | 9/2008 | Peters et al. |
| 2009/0312364 A1 | 12/2009 | Peters et al. |
| 2010/0029711 A1 | 2/2010 | Peter et al. |
| 2010/0227883 A1 | 9/2010 | Peters et al. |
| 2012/0088789 A1 | 4/2012 | Peters et al. |

FOREIGN PATENT DOCUMENTS

WO    WO 2007/093604 A1    8/2007

OTHER PUBLICATIONS

PCT/ISA/210—International Search Report mailed on Feb. 21, 2011, issued in PCT/EP2011/050455.
PCT/ISA/237—Written Opinion of International Searching Authority mailed on Feb. 21, 2011, issued in PCT/EP2011/050455.

*Primary Examiner* — Wu-Cheng Winston Shen
*Assistant Examiner* — Jean Cornet
(74) *Attorney, Agent, or Firm* — Birch, Stewart, Kolasch & Birch, LLP

(57) ABSTRACT

The present application discloses novel 8-aza-bicyclo[3.2.1] oct-3-yloxy)-chromen-2-one derivatives useful as monoamine neurotransmitter re-uptake inhibitors. In other aspects the application discloses the use of these compounds, a method for therapy and to pharmaceutical compositions comprising these compounds.

3 Claims, No Drawings

CHROMEN-2-ONE DERIVATIVES AND THEIR USE AS MONOAMINE NEUROTRANSMITTER RE-UPTAKE INHIBITORS

CROSS REFERENCE TO RELATED APPLICATIONS

This application is a Continuation of application Ser. No. 13/575,712, filed on Oct. 12, 2012. Application Ser. No. 13/575,712 is the U.S. National Phase Application of International No. PCT/EP2011/050455, filed on Jan. 14, 2011, which claims priority under 35 U.S.C. 119(e) to U.S. Provisional Application No. 61/301,367, filed on Feb. 4, 2010. Priority is also claimed to Danish Patent Application No. PA 2010 00079, filed in Denmark on Jan. 29, 2010. The disclosures of all of the foregoing applications are hereby expressly incorporated by reference into the present application.

TECHNICAL FIELD

This invention relates to novel 8-aza-bicyclo[3.2.1]oct-3-yloxy)-chromen-2-one derivatives useful as monoamine neurotransmitter re-uptake inhibitors.

In other aspects the invention relates to the use of these compounds in a method for therapy and to pharmaceutical compositions comprising the compounds of the invention.

BACKGROUND ART

Serotonin Selective Reuptake Inhibitors (SSRIs) currently provide efficacy in the treatment of several CNS disorders, including depression and panic disorder. SSRIs are generally perceived by psychiatrists and primary care physicians as effective, well-tolerated and easily administered. However, they are associated with a number of undesirable features.

Thus, there is still a strong need for compounds with an optimised pharmaco-logical profile as regards the activity on reuptake of the monoamine neurotransmitters serotonin, dopamine and noradrenaline, such as the ratio of the noradrenaline reuptake versus the serotonine and dopamine reuptake activity.

WO 2006/035034 (NeuroSearch A/S), and WO 2007/093604 (NeuroSearch NS) describes various chromen-2-one-yl derivatives, useful as monoamine neurotransmitter re-uptake inhibitors.

SUMMARY OF THE INVENTION

It is an object of the invention to provide novel compounds which show activity as monoamine neurotransmitter re-uptake inhibitors.

In one aspect, the invention provides a compound of Formula (I):

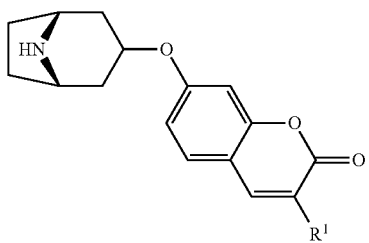

or a pharmaceutically acceptable salt thereof; wherein $R^1$ is as defined below.

In another aspect, the invention provides a pharmaceutical composition, comprising a therapeutically effective amount of a compound of the invention, or a pharmaceutically acceptable salt thereof, together with at least one pharmaceutically acceptable carrier, excipient or diluent.

In another aspect, the invention provides the use of a compound of the invention, or a pharmaceutically acceptable salt thereof, for the manufacture of a pharmaceutical composition for the treatment, prevention or alleviation of a disease or a disorder or a condition of a mammal, including a human, which disease, disorder or condition is responsive to inhibition of monoamine neurotransmitter re-uptake in the central nervous system.

In another aspect, the invention relates to a method for treatment, prevention or alleviation of a disease or a disorder or a condition of a living animal body, including a human, which disorder, disease or condition is responsive to responsive to inhibition of monoamine neurotransmitter re-uptake in the central nervous system, which method comprises the step of administering to such a living animal body in need thereof a therapeutically effective amount of a compound of the invention, or a pharmaceutically acceptable salt thereof.

Another embodiment of the invention is the provision of compounds with optimal pharmacodynamic and/or pharmacokinetic properties such as kinetic behavior, bioavailability, solubility, efficacy and/or adverse effects.

Other objects of the invention will be apparent to the person skilled in the art from the following detailed description and examples.

DETAILED DISCLOSURE OF THE INVENTION

In one aspect the present invention provides compounds of Formula (I):

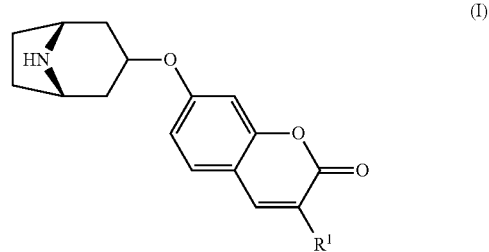

or a pharmaceutically acceptable salt thereof, wherein $R^1$ represents methoxy.

In another embodiment of the invention, the compound of the invention is exo-7-[(-8-azabicyclo[3.2.1]octan-3-yl)oxy]-3-methoxy-chromen-2-one; or a pharmaceutically acceptable salt thereof.

DEFINITION OF SUBSTITUENTS

As used throughout the present specification and appended claims, the following terms have the indicated meaning:

The term "$C_{1-6}$-alkyl" as used herein means a saturated, branched or straight hydrocarbon group having from 1-6 carbon atoms, e.g. $C_{1-3}$-alkyl, $C_{1-4}$-alkyl, $C_{1-6}$-alkyl, $C_{2-6}$-alkyl, $C_{3-6}$-alkyl, and the like. Representative examples are methyl, ethyl, propyl (e.g. prop-1-yl, prop-2-yl (or iso-propyl)), butyl (e.g. 2-methylprop-2-yl (or tert-butyl), but-1-yl, but-2-yl), pentyl (e.g. pent-1-yl, pent-2-yl, pent-3-yl), 2-methylbut-1-yl, 3-methylbut-1-yl, hexyl (e.g. hex-1-yl), heptyl (e.g. hept-1-yl), octyl (e.g. oct-1-yl), nonyl (e.g. non-1-yl), and the like.

The term "$C_{1-6}$-alkoxy" as used herein refers to the radical $C_{1-6}$-alkyl-O—. Representative examples are methoxy, ethoxy, propoxy (e.g. 1-propoxy, 2-propoxy), butoxy (e.g. 1-butoxy, 2-butoxy, 2-methyl-2-propoxy), pentoxy (1-pentoxy, 2-pentoxy), hexoxy (1-hexoxy, 3-hexoxy), and the like.

The term "treatment" as used herein means the management and care of a patient for the purpose of combating a disease, disorder or condition. The term is intended to include the delaying of the progression of the disease, disorder or condition, the alleviation or relief of symptoms and complications, and/or the cure or elimination of the disease, disorder or condition. The patient to be treated is preferably a mammal, in particular a human being.

The terms "disease", "condition" and "disorder" as used herein are used interchangeably to specify a state of a patient which is not the normal physiological state of man.

The term "medicament" as used herein means a pharmaceutical composition suitable for administration of the pharmaceutically active compound to a patient.

The term "pharmaceutically acceptable" as used herein means suited for normal pharmaceutical applications, i.e. giving rise to no adverse events in patients etc.

The term "effective amount" as used herein means a dosage which is sufficient in order for the treatment of the patient to be effective compared with no treatment.

The term "therapeutically effective amount" of a compound as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

Pharmaceutically Acceptable Salts

The compound of the invention may be provided in any form suitable for the intended administration. Suitable forms include pharmaceutically (i.e. physiologically) acceptable salts, and pre- or prodrug forms of the compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Examples of pharmaceutically acceptable cationic salts of a compound of the invention include, without limitation, the sodium, the potassium, the calcium, the magnesium, the zinc, the aluminium, the lithium, the choline, the lysinium, and the ammonium salt, and the like, of a compound of the invention containing an anionic group. Such cationic salts may be formed by procedures well known and described in the art.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the compound of the invention include examples of suitable prodrugs of the substances according to the invention include compounds modified at one or more reactive or derivatizable groups of the parent compound. Of particular interest are compounds modified at a carboxyl group, a hydroxyl group, or an amino group. Examples of suitable derivatives are esters or amides.

The compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Labelled Compounds

The compounds of the invention may be used in their labelled or unlabelled form. In the context of this invention the labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radionuclide as a label. Positron emitting radionuclides are all candidates for usage. In the context of this invention the radionuclide is preferably selected from $^2H$ (deuterium), $^3H$ (tritium), $^{11}C$, $^{13}C$, and $^{14}C$.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Methods of Preparation

The compounds of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

Compounds of the invention may be tested for their ability to inhibit reuptake of the monoamines dopamine, noradrenaline and serotonin in synaptosomes e.g. such as described in WO 97/30997 (NeuroSearch NS) or WO 97/16451 (NeuroSearch A/S). Based on the balanced activity observed in these tests the compound of the invention is considered useful for the treatment, prevention or alleviation of a disease or a disorder or a condition of a mammal, including a human, which disease, disorder or condition is responsive to inhibition of monoamine neurotransmitter re-uptake in the central nervous system.

In one embodiment, the compounds of the invention are considered useful for the treatment, prevention or alleviation of: mood disorder, depression, atypical depression, depression secondary to pain, major depressive disorder, dysthymic disorder, bipolar disorder, bipolar I disorder, bipolar II disorder, cyclothymic disorder, mood disorder due to a general medical condition, substance-induced mood disorder, pseudodementia, obsessive compulsive disorder, panic disorder, panic disorder without agoraphobia, panic disorder with agoraphobia, agoraphobia without history of panic disorder, panic attack, anxiety, generalized anxiety disorder, social anxiety disorder, social phobia, specific phobia, post-traumatic stress disorder, acute stress disorder, sleep disorders, obesity, eating disorder, anorexia nervosa, bulimia, memory deficits, memory loss, dementia, dementia of ageing, senile dementia, Alzheimer's disease, memory dysfunction in ageing, drug addiction, drug abuse, drug abuse liability, cocaine abuse, nicotine abuse, tobacco abuse, alcohol addiction, alcoholism, withdrawal symptoms caused by termination of use of addictive substances, premenstrual syndrome, premenstrual dysphoric disorder, late luteal phase syndrome, post-traumatic syndrome, chronic fatigue syndrome, persistent vegetative state, lameness, urinary incontinence, stress incontinence, urge incontinence, nocturnal incontinence, sexual dysfunction, erectile dysfunction, erectile difficulty, premature ejaculation, premature female orgasm, movement disorders, such as Parkinson's disease, parkinsonism, dystonia, restless leg syndrome, and periodic limb movement disorder; pervasive developmental disorders, Asperger's disorder, Rett's disorder, childhood disintegrative disorder, learning disabilities, attention deficit hyperactivity disorder (ADHD), motor skills disorders, mutism, trichotillomania, narcolepsy, post-stroke depression, stroke-induced brain damage, stroke-induced neuronal damage, Gilles de la Tourettes disease, tinnitus, tic disorders, body dysmorphic disorders, oppositional defiant disorder or post-stroke disabilities. In another embodiment, the compounds of the invention are considered useful for the treatment or alleviation of sexual dysfunction. In another embodiment, the compounds of the invention are considered useful for the treatment or alleviation of erectile dysfunction. In another embodiment, the compounds of the invention are considered useful for the treatment or alleviation of lameness. In another embodiment, the compounds of the invention are considered useful for the treatment or alleviation of restless leg syndrome. In another embodiment, the compounds of the invention are considered useful for the treatment or alleviation of dystonia. In another embodiment, the compounds of the invention are considered useful for the treatment or alleviation of Parkinson's disease. In another embodiment, the compounds of the invention are considered useful for the treatment or alleviation of depression. In another embodiment, the compounds of the invention are considered useful for the treatment or alleviation of anxiety. In another embodiment, the compounds of the invention are considered useful for the treatment or alleviation of pain, e.g. acute pain, chronic pain, mild pain, moderate or severe pain, postoperative pain, neuropathic pain, central neuropathic pain, pain related to diabetic neuropathy, to postherpetic neuralgia, to peripheral nerve injury, to phantom limb pain, to neurogenic inflammation, to fibromyalgia, to chronic regional pain syndrome, somatic pain, visceral pain or cutaneous pain, pain caused by inflammation or by infection, pain related to arthritis, osteoarthritis, rheumatoid arthritis, neuronal hyperexcitability disorders, peripheral nerve hyperexcitability, back pain, cancer pain, dental pain, irritable bowel pain, irritable bowel syndrome, post-operative pain, post-mastectomy pain syndrome (PMPS), post-stroke pain, drug-induced neuropathy, complex regional pain syndrome (CRPS), sympathetically maintained pain (SMP), trigeminal neuralgia, myofacial pain, chronic headache, migraine, migraine-related disorders or tension-type headache. In another embodiment, the compounds of the invention are considered useful for the treatment or alleviation of pain. In another embodiment, the compounds of the invention are considered useful for the treatment or alleviation of complex regional pain syndrome (CRPS).

It is at present contemplated that a suitable dosage of the active pharmaceutical ingredient (API) is within the range of from about 0.1 to about 1000 mg API per day, more preferred of from about 10 to about 500 mg API per day, most preferred of from about 30 to about 100 mg API per day, dependent, however, upon the exact mode of administration, the form in which it is administered, the indication considered, the subject and in particular the body weight of the subject involved, and further the preference and experience of the physician or veterinarian in charge.

Preferred compounds of the invention show a biological activity in the sub-micromolar and micromolar range, i.e. of from below 1 to about 100 µM.

Pharmaceutical Compositions

In another aspect the invention provides novel pharmaceutical compositions comprising a therapeutically effective amount of the compound of the invention.

While a compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In one embodiment, the invention provides pharmaceutical compositions comprising the compound of the invention, or a pharmaceutically acceptable salt or derivative thereof, together with one or more pharmaceutically acceptable carriers, and, optionally, other therapeutic and/or prophylactic ingredients, known and used in the art. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The compound of the invention can be administered in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from a compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets may contain from five or ten to about seventy percent of the active compound. Suitable carriers are magnesium carbonate, magnesium stearate, talc, sugar, lactose, pectin, dextrin, cellulose, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

In one embodiment, the invention provides tablets or capsules for oral administration.

In another embodiment, the invention provides liquids for intravenous administration and continuous infusion.

Further details on techniques for formulation and administration may be found in the latest edition of *Remington's Pharmaceutical Sciences* (Maack Publishing Co., Easton, Pa.).

The dose administered must of course be carefully adjusted to the age, weight and condition of the individual being treated, as well as the route of administration, dosage form and regimen, and the result desired, and the exact dosage should of course be determined by the practitioner.

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 μg/kg i.v. and 1 μg/p.o. The upper limit of the dosage range is presently considered to be about 10 mg/kg i.v. and 100 mg/kg p.o. Ranges are from about 0.1 μg/kg to about 10 mg/kg/day i.v., and from about 1 μg/kg to about 100 mg/kg/day p.o.

Methods of Therapy

In another aspect the invention provides a method for the treatment, prevention or alleviation of a disease or a disorder or a condition of a living animal body, including a human, which disease, disorder or condition is responsive to inhibition of monoamine neurotransmitter re-uptake in the central nervous system, and which method comprises administering to such a living animal body, including a human, in need thereof an effective amount of a compound of the invention.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

EXAMPLES

The following examples and general procedures refer to intermediate compounds and final products for general formula (I) identified in the specification. The preparation of the compounds of general formula (I) of the present invention is described in detail using the following examples. Occasionally, the reaction may not be applicable as described to each compound included within the disclosed scope of the invention. The compounds for which this occurs will be readily recognized by those skilled in the art. In these cases the reactions can be successfully performed by conventional modifications known to those skilled in the art, which is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may easily be prepared from known starting materials.

All reactions involving air sensitive reagents or intermediates are performed under nitrogen and in anhydrous solvents. Magnesium sulphate is used as drying agent in the workup-procedures and solvents are evaporated under reduced pressure.

The abbreviations as used in the examples have the following meaning:

DCM: Dichloromethane

EtOAc: Ethyl acetate

THF: Tetrahydrofuran

TEA: Triethylamine

Preparatory Examples endo-Benzoic acid
8-methyl-8-aza-bicyclo[3.2.1]oct-3-yl ester

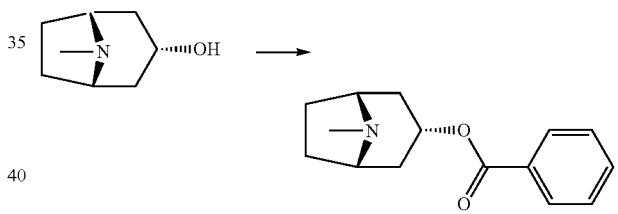

Benzoylchloride (84.3 g, 600 mmol) was added during 30 min at <30° C. to a mixture of tropine (70.6 g, 500 mmol), potassium tert-butoxide (67.3 g, 600 mmol) and THF (500 ml). The mixture was stirred at room temperature for 2 h. Water (1 L) was added followed by extraction with diethyl-ether (2×500 ml). The organic phase was washed twice with water (2×200 ml) followed by a solution of saturated aqueous sodium chloride (200 ml). The ether phase was dried and hydrochloric acid in ethanol (170 ml, 3 M) was added. The precipitated hydrochloride was filtered and washed with diethylether. The free base was obtained by adding an excess of aqueous ammonia followed by extraction with a mixture of ethylacetate and diethylether. Yield 66.8 g (54%).

endo-Benzoic acid 8-aza-bicyclo[3.2.1]oct-3-yl ester

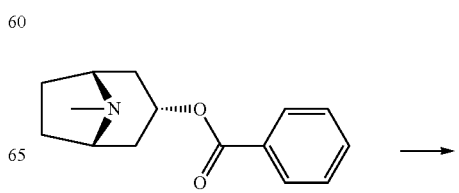

-continued

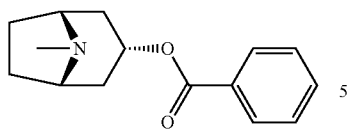

2,2,2-Trichloroethylchloroformate (75.0 ml, 544 mmol) was added dropwise to a mixture of endo-benzoic acid 8-methyl-8-aza-bicyclo[3.2.1]oct-3-yl ester (66.8 g, 272 mmol) and dry toluene (500 ml). The mixture was allowed to stir for 1 h at room temperature, followed by 15 h at 100° C. Water (250 ml) was added followed by stirring 1 h. The phases were separated and the organic phase was washed twice with water (2×200 ml). The mixture of the intermediate 3-benzoyloxy-8-aza-bicyclo[3.2.1]octane-8-carboxylic acid trichloromethyl ester, was dried and evaporated. Acetic acid (350 ml) was added followed by addition of zinc (53.4 g, 817 mmol) over 3 h time period. Water (100 ml) was added, cooled by adding ice and made alkaline by adding concentrated aqueous ammonia (ca: 400 ml) and the mixture was extracted with dichloromethane (2×300 ml). Yield 44.5 g (61%).

endo-3-Benzoyloxy-8-aza-bicyclo[3.2.1]octane-8-carboxylic acid tert-butyl ester

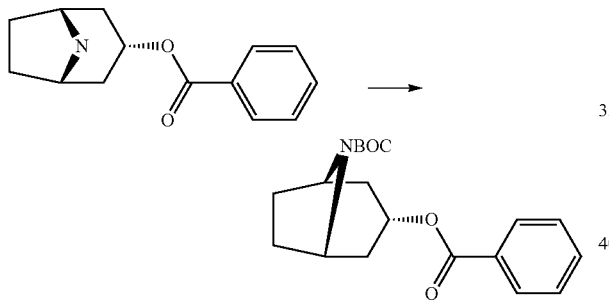

Di-tert-butyl-dicarbonate (39.9 g, 183 mmol) solved in THF (100 ml) was added to a stirred mixture of endo-benzoic acid 8-aza-bicyclo[3.2.1]oct-3-yl ester (44.5 g, 166.4 mmol), triethylamine (67.4 g, 666 mmol) and THF (250 ml) during 0.5 h at room temperature, followed by stirring for 1 h. Water (1 L) was added and the mixture was extracted with diethylether (2×300 ml). The collected ether phase was washed twice with water (2×200 ml), dried and evaporated. Yield 60.1 g (100%).

endo-3-Hydroxy-8-aza-bicyclo[3.2.1]octane-8-carboxylic acid tert-butyl ester

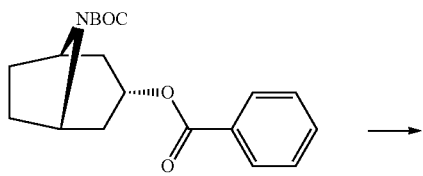

-continued

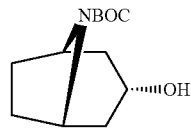

A mixture of endo-3-benzoyloxy-8-aza-bicyclo[3.2.1]octane-8-carboxylic acid tert-butyl ester (55.0 g, 166 mmol), potassium hydroxide (11.2 g 199 mmol) and ethanol (99%, 400 ml) was stirred for 3 days at room temperature. Potassium benzoate was separated by filtration and the filtrate was evaporated. Diethylether (200 ml) was added and remaining potassium benzoate was separated by filtration and the filtrate was evaporated. The product was triturated with petroleum. Yield 30.0 g (80%). Mp 139.5-140.8° C.

Example 1

Exo-tert-butyl-3-(3-methoxy-2-oxo-chromen-7-yl)oxy-8-azabicyclo[3.2.1]octane-8-carboxylate (Intermediate)

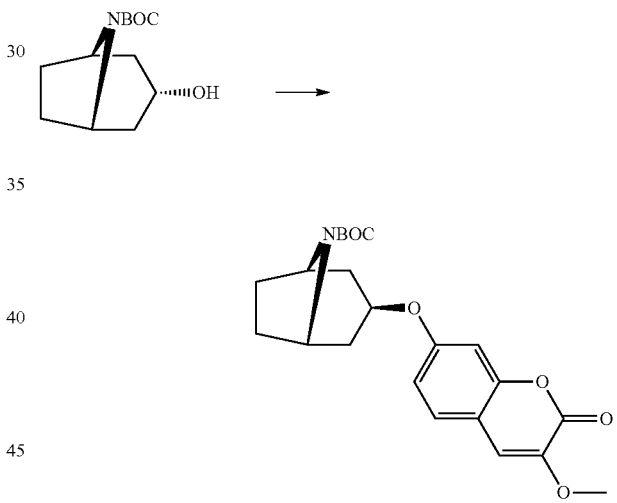

Triphenylphosphine (1.15 g, 4.37 mmol) was solved in toluene (20 ml) and cooled to <20° C. Diethylazodicarboxylate (40% in toluene) (2.0 ml, 4.37 mmol) was added to the mixture below 20° C., followed by stirring for 10 minutes. endo-3-Hydroxy-8-aza-bicyclo[3.2.1]octane-8-carboxylic acid tert-butyl ester (0.828 g, 3.64 mmol) was added and after 10 minutes 7-hydroxy-3-methoxy-chromen-2-one (0.70 g, 3.64 mmol) (prepared according to J. Med. Chem. 1999, 42, p 2662-2672) was added to the mixture. The temperature raised to 25° C. due to an exothermic reaction. The mixture precipitates. The mixture was allowed to stir for 15 h at room temperature. Water (20 ml) and sodium hydroxide (0.5 ml, 4 M) was added followed by stirring. The mixture was cooled on an ice-bath, filtered and washed with water and diethylether. Yield 0.92 g (63%).

Exo-7-[(-8-azabicyclo[3.2.1]octan-3-yl)oxy]-3-methoxy-chromen-2-one hydrochloride (Compound 1.1)

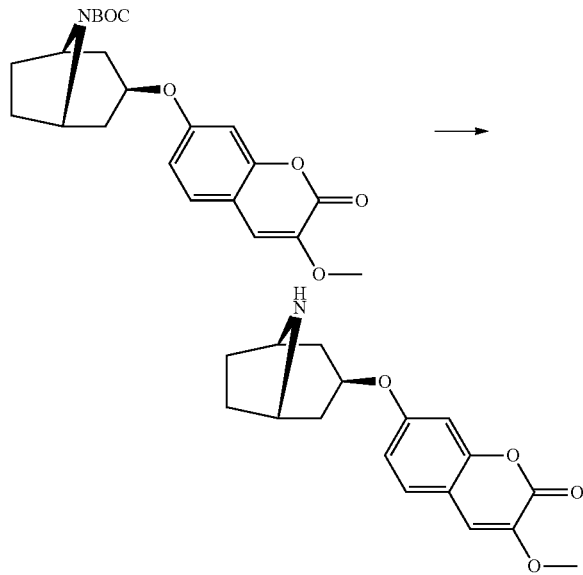

Exo-tert-butyl-3-(3-methoxy-2-oxo-chromen-7-yl)oxy-8-azabicyclo[3.2.1]octane-8-carboxylate (0.92 g, 2.29 mmol) and hydrogen chloride (15 ml, 1 M) in acetic acid was mixed as a solution and stirred at room-temperature and precipitated after a few minutes. The product was filtered and washed with diethylether. Yield 0.48 g (62%). LC-ESI-HRMS of [M+H]+ shows 302.13856 Da. Calc. 302.138689 Da, dev. −0.4 ppm.

In Vitro Inhibition Activity

Compounds were tested for their ability to inhibit the reuptake of the monoamine neurotransmitters dopamine (DA) noradrenaline (NA) and serotonine (5-HT) in synaptosomes as described in WO 97/16451 (NeuroSearch A/S).

The test values are given as $IC_{50}$ (the concentration (µM) of the test substance which inhibits the specific binding of $^3$H-DA, $^3$H-NA, or $^3$H-5-HT by 50%).

Test results obtained by testing the compound of the present invention appear from the below table:

TABLE 1

| Test compound | 5-HT-uptake $IC_{50}$(µM) | DA-uptake $IC_{50}$(µM) | NA-uptake $IC_{50}$(µM) |
|---|---|---|---|
| 1.1 | 0.0029 | 0.07 | 0.0038 |

From the foregoing it will be appreciated that, although specific embodiments of the invention have been described herein for purposes of illustration, various modifications may be made without deviating from the spirit and scope of the invention. Accordingly, the invention is not to be limited as by the appended claims.

The features disclosed in the foregoing description, in the claims and/or in the accompanying drawings, may both separately and in any combination thereof, be material for realising the invention in diverse forms thereof.

What is claimed is:

1. A compound of Formula (I):

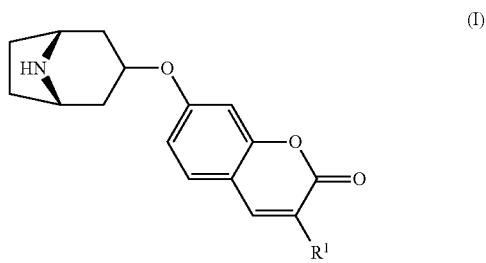

wherein $R^1$ is methoxy, or a pharmaceutically acceptable salt thereof.

2. The compound according to claim 1, which is exo-7-[(-8-azabicyclo[3.2.1]octan-3-yl)oxy]-3-methoxy-chromen-2-one hydrochloride.

3. A pharmaceutical composition, comprising a therapeutically effective amount of a compound, or a pharmaceutically acceptable salt thereof according to claim 1, together with at least one pharmaceutically acceptable carrier, excipient or diluent.

* * * * *